United States Patent
Perry

(10) Patent No.: US 6,688,305 B1
(45) Date of Patent: Feb. 10, 2004

(54) THERAPEUTIC AID

(76) Inventor: Doreen L. Perry, RR #1, Corbeil, Ontario (CA), P0H 1K0

(*) Notice: Subject to any disclaimer, the term of this patent is extended or adjusted under 35 U.S.C. 154(b) by 0 days.

(21) Appl. No.: 10/138,943

(22) Filed: May 3, 2002

(51) Int. Cl.[7] ............................ A61M 15/00; A62B 7/00
(52) U.S. Cl. ............................ 128/202.16; 128/202.17; 128/202.18; 128/203.12
(58) Field of Search .................. 128/200.14, 200.23, 128/200.24, 204.11, 204.12, 204.13, 203.12, 202.16, 202.17, 202.18

(56) References Cited

U.S. PATENT DOCUMENTS

| | | | |
|---|---|---|---|
| D50,649 S | | 4/1917 | Day |
| 4,606,328 A | * | 8/1986 | Thoman ..................... 600/27 |
| 4,694,829 A | | 9/1987 | Frye |
| 4,763,604 A | * | 8/1988 | Meekins ..................... 119/28.5 |
| 4,826,479 A | | 5/1989 | Burgin et al. |
| 4,955,945 A | | 9/1990 | Weick |
| 4,969,869 A | | 11/1990 | Burgin et al. |
| 5,038,431 A | * | 8/1991 | Burgin et al. ................. 5/641 |
| 5,299,335 A | * | 4/1994 | Ivester et al. ................. 5/641 |
| 5,542,122 A | | 8/1996 | Moldovan |
| 5,690,096 A | * | 11/1997 | Burch ..................... 128/204.18 |
| 5,819,347 A | * | 10/1998 | Masuda ..................... 5/641 |
| 5,853,002 A | * | 12/1998 | Kawasaki ............... 128/200.14 |
| 5,868,131 A | * | 2/1999 | Murchie ................. 128/204.13 |
| 6,090,403 A | * | 7/2000 | Block et al. ................. 424/447 |
| 6,193,577 B1 | * | 2/2001 | Kaplan ..................... 446/72 |
| 6,244,265 B1 | * | 6/2001 | Cronk et al. ........... 128/200.24 |
| 6,276,360 B1 | * | 8/2001 | Cronk et al. ........... 128/200.24 |
| 6,295,982 B1 | * | 10/2001 | Reed, Jr. ............... 128/200.24 |
| 6,343,968 B1 | * | 2/2002 | Louie et al. ................. 446/72 |
| 6,430,764 B1 | * | 8/2002 | Peters ........................... 5/641 |

* cited by examiner

Primary Examiner—Weilun Lo
Assistant Examiner—Michael G. Mendoza

(57) ABSTRACT

A therapeutic aid for providing therapeutic vapors to a child having cold symptoms. The therapeutic aid includes a body member having a perimeter wall. The perimeter wall defines an interior space. The perimeter wall of the body member has a slot positioned along a front portion of the body member whereby the slot is for permitting access to the interior space of the body member. A treatment member is insertable into the interior space of the body member. The treatment member is designed for emitting therapeutic vapors through the body member for easing the cold symptoms of the child when the body member is positioned in a proximity to the child.

1 Claim, 2 Drawing Sheets

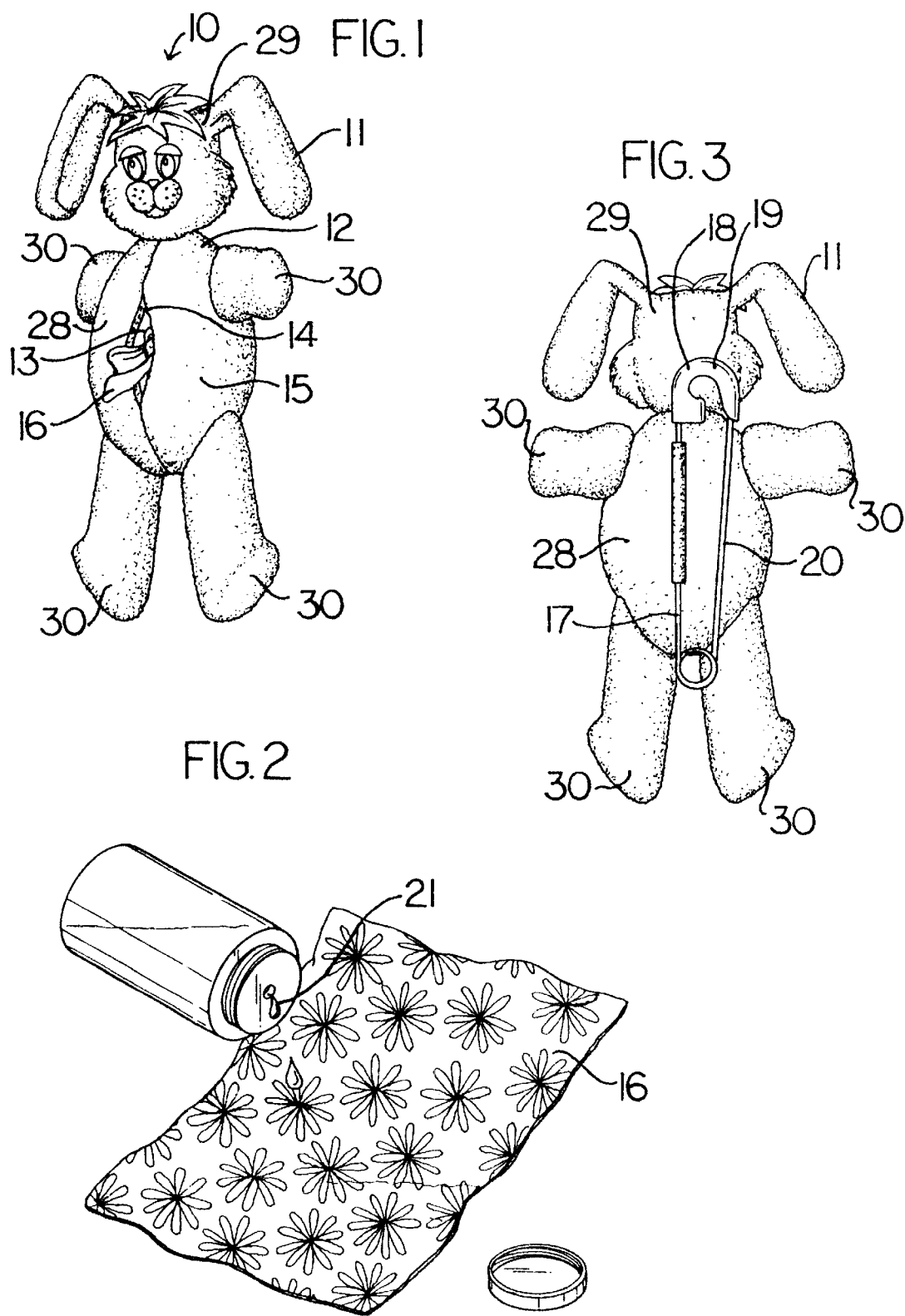

THERAPEUTIC AID

BACKGROUND OF THE INVENTION

1. Field of the Invention

The present invention relates to therapeutic stuffed toys and more particularly pertains to a new therapeutic aid for providing therapeutic vapors to a child having cold symptoms.

2. Description of the Prior Art

The use of therapeutic stuffed toys is known in the prior art. U.S. Pat. No. 4,694,829 describes an apparatus for stuffed toy that provides a hot or cold compress for a child. Another type of therapeutic stuffed toy is U.S. Pat. No. 5,542,122 having an article of apparel having a stuffed toy secured thereto for an ornamental appearance. A type of vapor dispenser is U.S. Pat. No. 4,955,945 having a flat dish the is positionable under the nostrils of the user for providing therapeutic vapors to the nostrils of the user. A type of therapeutic medication dispenser is U.S. Pat. No. 4,969,869 having a pillow that is permeable by therapeutic gases for treating a user. A type of stuffed toy is U.S. Pat. No. Des. 50,649 showing an effigy.

While these devices fulfill their respective, particular objectives and requirements, the need remains for a device that has certain improved features having a reusable therapeutic member that is comforting to a child and inhibits direct contact of the child with the therapeutic member.

SUMMARY OF THE INVENTION

The present invention meets the needs presented above by providing a body member that has an interior space that the therapeutic member is inserted into and the body member is shaped like an animal to comfort the child.

Still yet another object of the present invention is to provide a new therapeutic aid that provides therapeutic vapors to help relieve the cold symptoms of a child.

Even still another object of the present invention is to provide a new therapeutic aid that has a body member that is comforting to the child.

To this end, the present invention generally comprises a body member having a perimeter wall. The perimeter wall defines an interior space. The perimeter wall of the body member has a slot positioned along a front portion of the body member whereby the slot is for permitting access to the interior space of the body member. A treatment member is insertable into the interior space of the body member. The treatment member is designed for emitting therapeutic vapors through the body member for easing the cold symptoms of the child when the body member is positioned in a proximity to the child.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a front perspective view of a new therapeutic aid according to the present invention.

FIG. 2 is rear perspective view of the present invention.

FIG. 3 is a perspective view of the therapeutic member of the present invention.

DESCRIPTION OF THE PREFERRED EMBODIMENT

Figure 4:
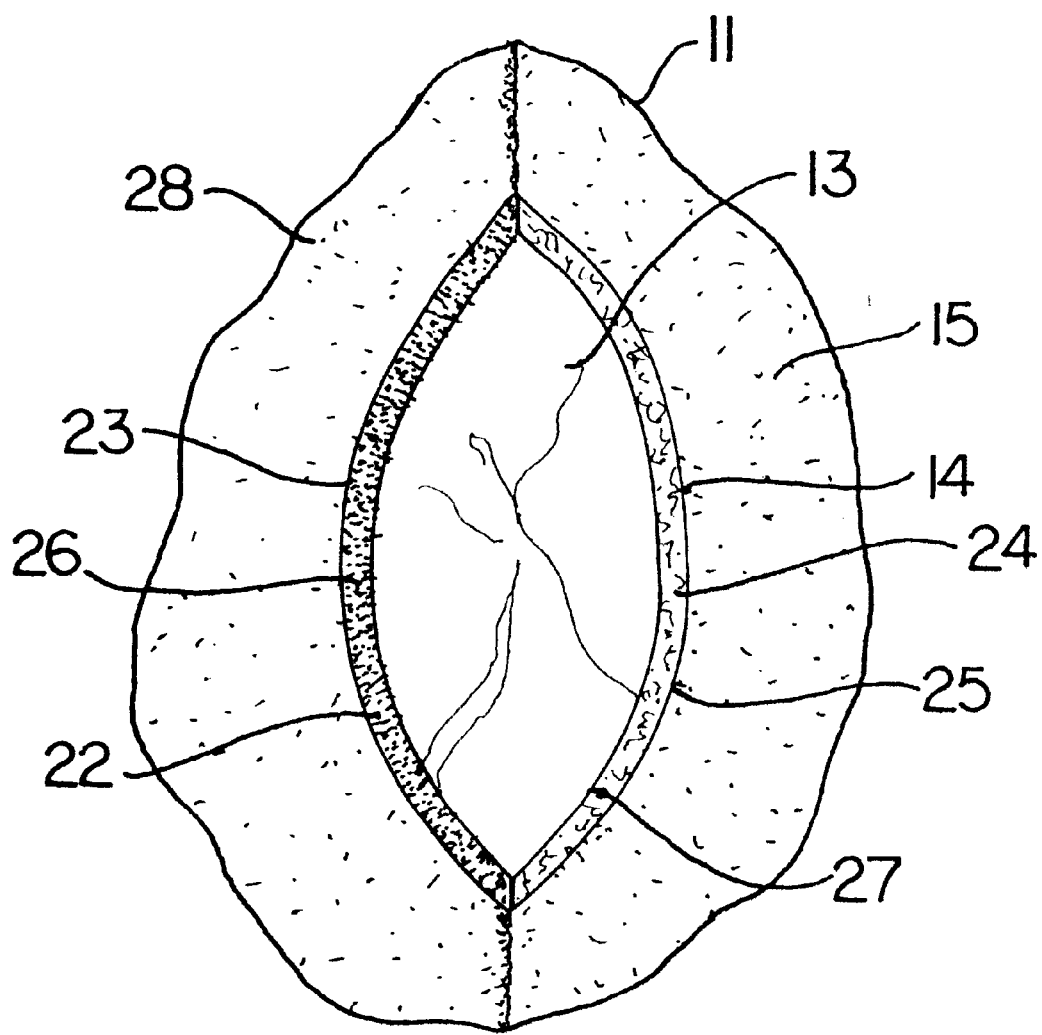
FIG. 4 is an enlarged front view of the slot of the perimeter wall of the body member of the present invention.

With reference now to the drawings, and in particular to FIGS. 1 through 4 thereof, a new therapeutic aid embodying the principles and concepts of the present invention and generally designated by the reference numeral 10 will be described.

As best illustrated in FIGS. 1 through 4, the therapeutic aid 10 generally comprises a body member 11 having a perimeter wall 12. The perimeter wall 12 defines an interior space 13. The perimeter wall 12 of the body member 11 has a slot 14 positioned along a front portion 15 of the body member 11 whereby the slot 14 is for permitting access to the interior space 13 of the body member 11.

A treatment member 16 is insertable into the interior space 13 of the body member 11. The treatment member 16 is designed for emitting therapeutic vapors through the body member 11 for easing the cold symptoms of the child when the body member 11 is positioned in a proximity to the child.

A fastening member 17 is coupled to the perimeter wall 12 of the body member 11. The fastening member 17 is designed for selectively securing the body member 11 to an article whereby the body member 11 is maintained in proximity to the child. The fastening member 17 comprises a safety pin 18. The safety pin 18 has a hooded portion 19 for selectively receiving a pin portion 20 whereby the hooded portion 19 is designed for preventing the pin portion 20 from impaling a user when the pin portion 20 is received by the hooded portion 19.

The treatment member 16 is substantially planar. The treatment member 16 comprises a flexible absorbent material. The flexible absorbent material absorbs a medicinal mixture 21 whereby the medicinal mixture 21 evaporates from the treatment member 16 for easing the cold symptoms of the child when the treatment member 16 is positioned in the interior space 13 of the body member 11. The body member 11 comprises a permeable material whereby said permeable material permits vapors from the evaporating medicinal mixture 21 to permeate out of the body member 11. The medicinal mixture 21 can comprise eucalyptus, camphor and alcohol to help ease the breathing of a child that is congested from a cold.

A first fastener 22 is coupled to a first face 23 of the slot 14. A second fastener 24 is coupled to a second face 25 of the slot 14 whereby the first fastener 22 is complimentary to the second fastener 24 for selectively closing the slot 14 of the perimeter wall 12 of the body member 11. The first fastener 22 comprises a first portion of hook and loop fastener 26. The second fastener 24 comprises a second portion of hook and loop fastener 27 whereby the second portion of hook and loop fastener 27 is complimentary to the first portion of hook and loop fastener 26 for selectively closing the slot 14 in the perimeter wall 12 of the body member 11.

The body member 11 has a body portion 28, a head portion 29 and a plurality of appendage portions 30. The head portion 29 and the appendage portions 30 are coupled to the body portion 28 whereby the body member 11 is designed for resembling an animal that is comforting to the child.

In use, the user drips the medicinal mixture 21 onto the treatment member 16. The treatment member 16 is then placed into the interior space 13 of the body member 11 and the slot 14 is closed. The body member 11 is then attached with the fastener member proximate the child so that the child can breath in the vapors released by the treatment member 16. In an alternative, the child can remove treatment member 16 from the interior space 13 of the body member 11 through the slot 14 to breathe in a more concentrated dose of vapors from the treatment member 16. The child can the replace the treatment member 16 in the interior space 13 of the body member 11.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed:

1. A therapeutic aid for easing cold symptoms of a child, the therapeutic aid comprising:

a body member having a perimeter wall, said perimeter wall defining an interior space, said perimeter wall of said body member having a slot positioned along a front portion of said body member such that said slot is for permitting access to said interior space of said body member;

a treatment member being insertable into said interior space of said body member, said treatment member being adapted for emitting therapeutic vapors through said body member for easing the cold symptoms of the child when said body member is positioned in a proximity to the child;

a fastening member being coupled to said perimeter wall of said body member such that said fastening member is coupled to an exterior of said perimeter wall and a rear portion of said body member, said fastening member being adapted for selectively securing said body member to an article such that said body member is maintained in proximity to the child and said slot is readily accessible to remove and replace said treatment member;

said fastening member comprising a safety pin, said safety pin having a hooded portion for selectively receiving a pin-portion such that said hooded portion is adapted for preventing said pin portion from impaling a user when said pin portion is received by said hooded portion;

said treatment member being substantially planar, said treatment member comprising a flexible absorbent material, said flexible absorbent material absorbing a medicinal mixture such that said medicinal mixture evaporates from said treatment member for easing the cold symptoms of the child when said treatment member is positioned in said interior space of said body member;

a first fastener being coupled to a first face of said slot, a second fastener being coupled to a second face of said slot such that said first fastener is complimentary to said second fastener for selectively closing said slot of said perimeter wall of said body member;

said first fastener comprising a first portion of book and loop fastener, said second fastener comprising a second portion of hook and loop fastener such that said second portion of hook and loop fastener is complimentary to said first portion of hook and loop fastener for selectively closing said slot in said perimeter wall of said body member; and said body member having a body portion, a head portion and a plurality of appendage portions, said head portion and said appendage portions being coupled to said body portion such that said body member is adapted for resembling an animal that is comforting to the child.

* * * * *